(12) United States Patent
Lin et al.

(10) Patent No.: US 11,135,474 B2
(45) Date of Patent: Oct. 5, 2021

(54) CRANK APPARATUS, BICYCLE AND STATIONARY EXERCISE BICYCLE

(71) Applicant: Giant Manufacturing Co., Ltd., Taichung (TW)

(72) Inventors: Chung-Wei Lin, Taichung (TW); Hsaio-Wen Hsu, Taichung (TW); Chih-Hsiang Shen, Taichung (TW); Ching-Yao Lin, Taichung (TW)

(73) Assignee: Giant Manufacturing Co., Ltd., Taichung (TW)

( * ) Notice: Subject to any disclaimer, the term of this patent is extended or adjusted under 35 U.S.C. 154(b) by 0 days.

(21) Appl. No.: 16/226,679

(22) Filed: Dec. 20, 2018

(65) Prior Publication Data
US 2019/0201736 A1 Jul. 4, 2019

(30) Foreign Application Priority Data
Dec. 28, 2017 (TW) ................................ 106146329

(51) Int. Cl.
*A63B 21/00* (2006.01)
*A63B 22/06* (2006.01)
(Continued)

(52) U.S. Cl.
CPC .......... *A63B 22/0605* (2013.01); *A61B 5/224* (2013.01); *A63B 21/4034* (2015.10);
(Continued)

(58) Field of Classification Search
CPC ........ A63B 2022/0611; A63B 2209/02; A63B 2209/01; A63B 24/0062; A63B 21/4034;
(Continued)

(56) References Cited

U.S. PATENT DOCUMENTS 8,006,574 B2 8/2011 Meyer
8,505,393 B2 8/2013 Meyer
(Continued)

FOREIGN PATENT DOCUMENTS

CN 104039639 9/2014
CN 105818921 8/2016
(Continued)

OTHER PUBLICATIONS

"Search Report of Europe Counterpart Application", dated May 24, 2019, p. 1-p. 9.
(Continued)

*Primary Examiner* — Megan Anderson
(74) *Attorney, Agent, or Firm* — JCIPRNET (57) ABSTRACT

A crank apparatus includes a crank arm having at least one cavity on one of the surfaces of the crank arm, at least one thin material layer embedded within the at least one cavity and having an exposed outer surface, and at least one sensing element attached to the outer surface of the thin material layer. The crank arm is manufactured of a material with non-uniform strain characteristics, the thin material layer is manufactured of a material with uniform strain characteristics, the crank arm is adapted to be deformed by a force, the thin material layer is adapted to be deformed correspondingly with the deformation of the crank arm, the at least one sensing element is adapted to measure the corresponding strain of the thin material layer to measure the force applied on the crank arm. A bicycle and a stationary exercise bicycle equipped with the crank apparatus are further provided.

18 Claims, 10 Drawing Sheets

(51) Int. Cl.
*B62M 3/00* (2006.01)
*G01L 3/14* (2006.01)
*A61B 5/22* (2006.01)
*A63B 23/04* (2006.01)
*A63B 24/00* (2006.01)
*A63B 69/16* (2006.01)
*G01L 3/02* (2006.01)

(52) U.S. Cl.
CPC ...... *A63B 23/0476* (2013.01); *A63B 24/0062* (2013.01); *A63B 69/16* (2013.01); *B62M 3/00* (2013.01); *G01L 3/1457* (2013.01); *A63B 21/4049* (2015.10); *A63B 2022/0611* (2013.01); *A63B 2209/02* (2013.01); *A63B 2220/51* (2013.01); *A63B 2220/833* (2013.01); *G01L 3/02* (2013.01)

(58) Field of Classification Search
CPC . A63B 22/0605; A63B 23/0476; A63B 69/16; A63B 2220/833; A63B 2220/80; B62M 3/00; B62M 6/50; B62J 45/40; G01L 3/1457; G01L 3/02; G01L 5/225

See application file for complete search history.

(56) References Cited

U.S. PATENT DOCUMENTS

| | | |
|---|---|---|
| 9,417,144 B2 | 8/2016 | Lull et al. |
| 9,496,769 B2 | 11/2016 | Tetsuka |
| 9,581,508 B2 | 2/2017 | Tetsuka et al. |
| 10,060,738 B2 * | 8/2018 | Fyfe ............... A61B 5/6895 |
| 2011/0041626 A1 | 2/2011 | Tuulari et al. |
| 2013/0233092 A1 | 9/2013 | Tetsuka et al. |
| 2014/0165744 A1 | 6/2014 | Lull et al. |
| 2014/0182393 A1 | 7/2014 | Heinkel et al. |
| 2017/0065848 A1 | 3/2017 | Lull et al. |
| 2019/0099119 A1 * | 4/2019 | Wakeham ............ A61B 5/221 |

FOREIGN PATENT DOCUMENTS

| | | |
|---|---|---|
| CN | 106275226 | 1/2017 |
| EP | 1378433 | 1/2004 |
| JP | 2012045999 | 3/2012 |
| TW | I529095 | 4/2016 |
| TW | I540077 | 7/2016 |
| TW | I585379 | 6/2017 |
| WO | 2016030768 | 3/2016 |
| WO | 2017165448 | 9/2017 |

OTHER PUBLICATIONS

"Office Action of China Counterpart Application", dated Jun. 15, 2021, p. 1-p. 4.

* cited by examiner

CRANK APPARATUS, BICYCLE AND STATIONARY EXERCISE BICYCLE

CROSS-REFERENCE TO RELATED APPLICATION

This application claims the priority benefit of Taiwan application serial no. 106146329, filed on Dec. 28, 2017. The entirety of the above-mentioned patent application is hereby incorporated by reference herein and made a part of this specification.

BACKGROUND OF THE DISCLOSURE

Field of the Disclosure

The disclosure is related to a crank apparatus, a bicycle and a stationary exercise bicycle, and particularly to a crank apparatus and a bicycle and a stationary exercise bicycle using the crank apparatus.

Description of Related Art

Conventional bicycle power meter is designed by using a strain gauge that is attached to the surface of a crank to measure a pedaling torque. Such design uses the characteristic that the body of crank is twisted and the surface thereof is deformed after the crank is subjected to force, so that the change of strain characteristic of the strain gauge is converted as appropriate to obtain the pedaling torque.

However, when the crank is manufactured of carbon-fiber material, the following factors need to be taken into consideration when the strain gauge is to be attached to the surface formed of carbon-fiber material to measure the pedaling torque: (1) it is difficult for the strain gauge to be directly attached to the carbon-fiber material; known method is performed by applying a clear coat on the surface formed of carbon-fiber material to combine the surface with the strain gauge, but when the deformation amount of the carbon-fiber material is transmitted to the clear coat, the data measured by the strain gauge is distorted; (2) since the directions of each stacking layer of the carbon-fiber material are different, the torsion of the crank body and the deformation of the surface are uniformed, causing the change amount of strain characteristic obtained by the strain gauge is not linear enough.

Therefore, the accuracy of known strain gauge in measuring pedaling torque of the crank formed of carbon-fiber material is significantly reduced. Additionally, in order to increase measuring accuracy of known strain gauge, typically a specific calibrating process is performed before use, which causes inconvenience to users.

SUMMARY OF THE DISCLOSURE

The disclosure provides a crank apparatus, a bicycle and a stationary exercise bicycle, capable of improving measuring accuracy while increasing convenience for users.

A crank apparatus of the disclosure provides a crank arm, at least one thin material layer and at least one sensing element. The crank arm has at least one cavity on one of the surfaces of the crank arm. The at least one thin material layer is embedded into the at least one cavity and having an exposed outer surface. The at least one sensing element is attached to the outer surface of the thin material layer. The crank arm is manufactured of a material having non-uniform strain characteristic. The thin material layer is manufactured of a material having uniform strain characteristic. The crank arm is adapted to be subjected to force and deformed. The thin material layer is adapted to be deformed corresponding to the deformation of the crank arm. The at least one sensing element is adapted to measure the corresponding strain of the thin material layer to measure the force applied to the crank arm. The disclosure further provides a bicycle and a stationary exercise bicycle respectively provided with the crank apparatus.

According to an embodiment of the disclosure, the cavity of the crank arm includes a plurality of protruded walls respectively covering at least one edge of the thin material layer.

According to an embodiment of the disclosure, wherein the movement of the thin material layer along any three orthogonal axial directions in the crank arm is limited by the plurality of protruded walls.

According to an embodiment of the disclosure, the crank arm is a solid member.

According to an embodiment of the disclosure, the crank arm is a hollow member.

According to an embodiment of the disclosure, the crank arm is manufactured of composite material having non-uniform strain characteristic.

According to an embodiment of the disclosure, the composite material includes a non-metal-and-non-metal composite material, a non-metal-and-metal composite material, and a metal-and-metal composite material.

According to an embodiment to the disclosure, the material of the crank arm includes any one of carbon fiber, glass fiber, Kevlar fiber, Dyneema fiber, plant fiber, boron fiber, aramid fiber, silicon carbide fiber, asbestos fabrics, monocrystalline whisker, metal wire and hard particles or a composite material consisting of a mixture of any two of the above.

According to an embodiment of the disclosure, the thin material layer is a single material having uniform strain characteristic.

According to an embodiment of the disclosure, the material of the thin material layer includes metal, plastic or flexible glass.

According to an embodiment of the disclosure, the thin material layer is subjected to a surface treatment to form a roughened surface. The surface treatment may be performed by using any one of a sand-blasting process, a texture-treatment process, a laser-treatment process, a plasma-treatment process, a chemical-treatment process.

According to an embodiment of the disclosure, the thickness of the thin material layer is within a range between 0.1 mm and 1.85 mm.

According to an embodiment of the disclosure, the at least one sensing element is a strain gauge or a stress sensor.

According to an embodiment of the disclosure, the at least one strain gauge is disposed on the outer surface of the thin material layer in a uni-axial manner. The at least one strain gauge is adapted to measure the corresponding strain of the thin material layer along a uni-axial direction.

According to an embodiment of the disclosure, the number of the at least one strain gauge is at least two. The at least two strain gauges are disposed on the outer surface of the thin material layer in a bi-axial manner. The at least two strain gauges are adapted to measure the corresponding strain of the thin material layer along any two orthogonal axial directions.

According to an embodiment of the disclosure, the number of the at least one strain gauge is at least three. The at least three strain gauges are disposed on the outer surface of the thin material layer in a tri-axial manner. The at least three strain gauges are adapted to measure the corresponding strain of the thin material layer along three orthogonal axial directions.

According to an embodiment of the disclosure, the at least one strain gauge is disposed on the outer surface of the thin material layer in a quarter-bridge form.

According to an embodiment of the disclosure, the at least one strain gauge is disposed on the outer surface of the thin material layer in a half-bridge form.

According to an embodiment of the disclosure, the at least one strain gauge is disposed on the outer surface of the thin material layer in a full-bridge form.

A bicycle of the disclosure includes a frame and the crank apparatus. The frame includes a crank shaft. A crank arm is fixed on the crank shaft. The crank arm is adapted to be deformed by the force generated by user's pedaling.

A stationary exercise bicycle of the disclosure includes a frame and the crank apparatus. The frame includes a crank shaft. A crank arm is fixed on the crank shaft. The crank arm is adapted to be deformed by the force generated by user's pedaling.

Based on the above, in the crank apparatus, the bicycle and the stationary exercise bicycle of the disclosure, the thin material layer is embedded into the cavity of the crank arm and having an exposed outer surface. The at least one sensing element is further attached to the outer surface exposed by the thin material layer. The crank arm is manufactured of a material having non-uniform strain characteristic. The thin material layer is manufactured of a material having uniform strain characteristic. The crank arm is adapted to be deformed by being subjected to force. The thin material layer is adapted to be deformed corresponding to the deformation of the crank arm. The at least one sensing element is adapted to measure the corresponding strain of the thin material layer to measure the force applied to the crank arm. By using the sensing element to directly measure the thin material layer having the material with uniform strain characteristic, it is possible to increase the accuracy of the sensing element in measuring the corresponding strain of the thin material layer, thereby accurately calculating the pedaling force applied to the crank arm. Additionally, by using the sensing element to directly measure the thin material layer having the material with uniform strain characteristic, the user can skip the action of calibrating the sensing element, such that it is more convenient for the user to use the bicycle with enhanced exercise experience.

In order to make the aforementioned features and advantages of the disclosure more comprehensible, embodiments accompanying figures are described in detail below.

DESCRIPTION OF EMBODIMENTS

Figure 1A:
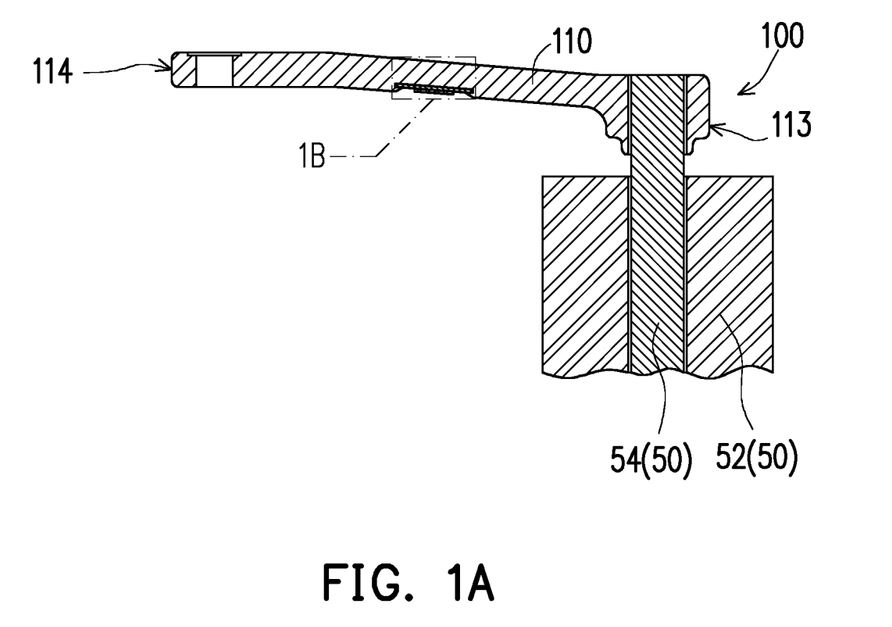
FIG. 1A is a schematic cross-sectional view of a crank apparatus according to an embodiment of the disclosure.
Figure 1B:
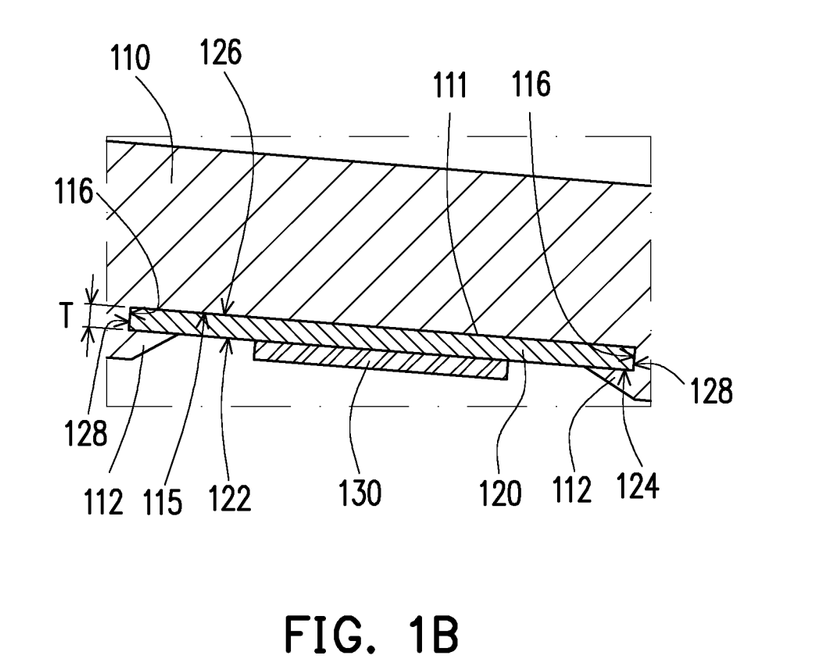
FIG. 1B is an enlarged view of the portion, labeled '1B' of FIG. 1A.

FIG. 1A is a schematic cross-sectional view of a crank apparatus according to an embodiment of the disclosure. FIG. 1B is an enlarged view of the portion, labeled '1B' of FIG. 1A. Referring to FIG. 1A and FIG. 1B, a crank apparatus 100 includes a crank arm 110, at least one thin material layer 120 and at least one sensing element 130. The crank arm 110 can be formed with at least one cavity 111 on at least one of the surfaces in the manufacturing process, and the cavity 111 can be communicated with the outer environment. The thin material layer 120 is embedded into the cavity 111, and the thin material layer 120 having an exposed outer surface 122. The sensing element 130 is attached to the outer surface 122 exposed by the thin material layer 120. The crank arm 110 is manufactured of a material having non-uniform strain characteristic. The thin material layer 120 is manufactured of a material having uniform strain characteristic. The crank arm 110 may be deformed by being subjected to force. The thin material layer 120 may be deformed corresponding to the deformation generated by the crank arm 110. The sensing element 130 may measure the force applied to the crank arm 110 through the thin material layer 120. In the embodiment, the disclosure provides no limitation to the position and the number of the cavity 111 disposed on the crank arm 110, and the position and the number of the thin material layer 120 may be set corresponding to the position and the number of the cavity 111 depending on the needs.

The crank apparatus 100 of the embodiment may be disposed on a bicycle, a stationary exercise bicycle or other facility suitable for pedaling, the disclosure provides no limitation thereto. For example, the crank apparatus 100 may be disposed on a bicycle 50. The bicycle 50 may include a frame 52. The frame 52 further includes a crank shaft 54 rotatably disposed thereon. A fixing end 113 of the crank arm 110 is fixed on the crank shaft 54 of the frame 52 to rotate along with the crank shaft 54. A pedaling end 114 of the crank arm 110 may be provided with a pedal (not shown) for the user to pedal. When the user pedals on the pedal (not shown), the crank arm 110 is subjected to force and deformed. Along with the crank arm 110 which is deformed by pedaling force, therefore the thin material layer 120 to be embedded into the crank arm 110 is squeezed or stretched accordingly. Since the thin material layer 120 is embedded into the cavity 111, each of the surfaces between the crank arm 110 and the thin material layer 120 has complete and good contact with each other, such that the force applied to the crank arm 110 can be smoothly transmitted to the thin material layer 120. Besides, since the thin material layer 120 has uniform strain characteristic (or referred to as isotropy), the deformation generated by the thin material layer 120 after being subjected to force is uniform, thereby improving accuracy of the sensing element 130 in measuring the torque of the crank arm 110. Accordingly, the pedaling force applied to the crank arm 110 can be calculated accurately such that the sensing element 130 can measure the corresponding strain of the thin material layer 120 more accurately. In other words, the target measured by the sensing element 130 is the crank arm 110 having the material with non-uniform strain characteristic (or referred to as anisotropy). The thin material layer 120 serves as a medium that transfers the force applied to the crank arm 110 to the sensing element 130. With the thin material layer 120, the non-uniform deformation transferred from the crank arm 110 to the sensing element 130 can be changed and become isotropic by using the embedded thin material layer 120 described above, thereby improving the accuracy of the sensing element 130 in measuring the torque of the crank arm 110. In this manner, it is possible to avoid the problem of distorted data caused by conventional sensing element that directly measures the crank arm having the material with non-uniform strain characteristic (or referred to as anisotropy). Additionally, since the thin material layer 120 inherently has uniform strain characteristic, after the crank apparatus 100 of the disclosure is disposed on the bicycle 50, it is not required to perform any additional calibrating action to the sensing element 130, and thus it is more convenient for the user to use the bicycle with enhanced exercise experience.

In the embodiment, the crank arm 110 may be manufactured of composite material with non-uniform strain characteristic (or referred to as anisotropy). For example, the material applied to the composite material with non-uniform strain characteristic may include any one of ceramics, graphite, rubber, synthetic resin, carbon, carbon fiber, glass fiber, Kevlar fiber, Dyneema fiber, plant fiber, boron fiber, aramid fiber, silicon carbide fiber, asbestos fabrics, monocrystalline whisker, metal wire, hard particles, aluminum, magnesium, copper and titanium or a composite material consisting of a mixture of at least two of the above materials. The disclosure provides no limitation to the material of the crank arm 110. The composite material having non-uniform strain characteristic may be a non-metal-and-non-metal composite material, a non-metal-and-metal composite material and a metal-and-metal composite material as long as the material has non-uniform strain characteristic (or referred to as anisotropy). In other words, when a force is applied to the crank arm 110, there is no specific relationship between the structural tensile amount or the compressive amount on the force-applying point of the crank arm 110 and the force-applying direction, and the tensile amount or the compressive amount is changed irregularly in various directions.

In the embodiment, the thin material layer 120 is a single material having uniform strain characteristic (or referred to as isotropy). For example, the material of the thin material layer 120 includes metal, plastic or flexible glass. The disclosure provides no limitation to the material of the thin material layer 120 as long as the material has uniform strain characteristic (or referred to as isotropy). In other words, when the same force is applied to the thin material layer 120 in various directions, the tensile amount or the compressive amount of the thin material layer 120 in different force-applying directions is all the same. In the embodiment, a preferable thickness T of the thin material layer 120 is within a range between 0.1 mm and 1.85 mm, and the thin material layer 120 may be subjected to a surface treatment to form a roughened surface, such that the thin material layer 120 can be more engaged and secured when being embedded into and clamped on the surface (i.e., at least one cavity 111 formed naturally in the manufacturing process) of the crank arm 110, which contributes effective transmission of strain force. The surface treatment process is performed, for example, by using any one of a sand-blasting process, a texture-treatment process, a laser-treatment process, a plasma-treatment process, a chemical-treatment process.

In the embodiment, the cavity 111 of the crank arm 110 includes a plurality of protruded walls 112. The protruded walls 112 block a portion of the cavity 111 and cover at least one edge 124 of the thin material layer 120. The movement of the thin material layer 120 along any three orthogonal axial directions (i.e., spatial coordinates X, Y, Z) in the cavity 111 of the crank arm 110 is limited by the protruded walls 112; that is, the thin material layer 120 is clamped and embedded into the cavity 111 that is formed as a recess on the surface of the crank arm 110. In other words, the protruded walls 112 cover the edge 124 of the thin material layer 120, such that the thin material layer 120 is firmly embedded into the cavity 111 of the crank arm 110.

In the embodiment, the crank arm 110 further includes a surface 115 and a plurality of surfaces 116. The surface 115 and the plurality of surfaces 116 define the cavity 111 together. The surface 115 and the protruded wall 112 are opposite to each other, and the surfaces 116 are respectively connected between the surface 115 and the protruded wall 112. Each of the protruded walls 112 covers the edge of the cavity 111. In other words, each orthogonal projection of the protruded wall 112 projected onto the surface 115 of the crank arm 110 along the direction of the thickness T of the thin material layer 120 is surrounded within the surfaces 116 in the cavity 111.

The thin material layer 120 has an embedded surface 126 and a plurality of lateral surfaces 128. The embedded surface 126 is disposed on another surface of the thin material layer 120 relatively away from the outer surface 122. The lateral surfaces 128 are respectively connected between the outer surface 122 and the embedded surface 126. In the embodiment, the cavity 111 of the crank arm 110 is a quadrilateral shape, that is, includes four surfaces 116. The crank arm 110 defines the cavity 111 with one surface 115, four surfaces 116 and four protruded walls 112 together. However, in other embodiments, the cavity may be defined by a polygonal shape having other shapes; the disclosure provides no limitation to the shape of the cavity as long as it is ensured that the thin material layer 120 is firmly embedded into the cavity without causing any displacement.

In the embodiment, the sensing element 130 is a strain gauge, but the sensing element may be a stress sensor in other embodiments. The number of the at least one sensing element 130 is exemplified as one, and disposed on the outer surface 122 of the thin material layer 120 in a uni-aixal manner to be adapted to measure the corresponding strain of the thin material layer 120 along the uni-axial direction, i.e., the changes of applied force at different positions along one of the single direction of the spatial coordinates X, Y, Z, thereby measuring the tensile strain, the compressive strain or the torsion strain of the thin material layer 120. However, the disclosure provides no limitation to the number of the sensing element, and the configuration number of the sensing element may be selected depending on actual needs for measurement. In other embodiments, the sensing element 130 may be disposed on the outer surface 122 of the thin material layer 130 in a bi-axial manner or a tri-axial manner, i.e., the changes of applied force at different positions along two directions of the spatial coordinates X, Y, Z. Moreover, the number of the sensing element is correspondingly plural corresponding to different configurations. For example, in other embodiments, the number of the sensing element disposed on the outer surface of the thin material layer may be at least two. The at least two sensing elements are disposed on the outer surface of the thin material layer in a bi-axial manner to be adapted to measure the corresponding strain of the thin material layer along any two orthogonal axial directions, thereby obtaining the tensile strain, the compressive strain, the Poisson's ratio or torsion change of the thin material layer. The sensing element may be selected from a plurality sets of sensing elements that are disposed in a bi-axial manner depending on the needs in actual configuration. For example, in other embodiments, the number of the sensing element that is disposed on the outer surface of the the thin material layer may be at least three. The at least three sensing elements are disposed on the outer surface of the thin material layer in a tri-axial manner to be adapted to measure the corresponding strain of the thin material layer along any three orthogonal axial directions, thereby measuring the tensile strain, the compressive strain, the torsion strain, the Poisson's ratio or component of strain of the thin material layer along different directions. The sensing element may be selected from a plurality sets of sensing elements disposed in a tri-axial manner depending on the needs in actual configuration.

In the embodiment, the number of the at least one sensing element 130 is one, for example, and disposed on the outer surface 112 of the thin material layer 120 in a quarter-bridge form, the disclosure provides no limitation to the number of the sensing element 130. The configuration number of the sensing element 130 may be selected depending on actual needs. In other embodiments, the sensing element 130 may be disposed on the outer surface 112 of the thin material layer 120 in a half-bridge form or a full-bridge form selectively depending on the requirement for measuring sensitivity. For example, in other embodiments, the number of the sensing element disposed on the outer surface of the thin material layer may be at least two. The at least two sensing elements are disposed on the outer surface of the thin material layer in a half-bridge form. The sensing element is disposed in a half-bridge form. In actual configuration, the sensing element may be selected from a plurality sets of sensing elements that are disposed in a half-bridge form depending on the needs. For example, in other embodiments, the number of the sensing element that is disposed on the outer surface of the thin material layer may be at least four. The at least four sensing elements are disposed on the outer surface of the thin material layer in a full-bridge form. In actual configuration, the sensing element may be selected from a plurality sets of sensing elements that are disposed in a full-bridge form depending on the needs; the disclosure provides no limitation thereto.

In the embodiment, the crank arm 110 is a solid member, but the crank arm may be a hollow member in other embodiments. FIG. 3A to FIG. 3C is a schematic view of a manufacturing process of the crank apparatus in FIG. 1A, and such manufacturing process is also applicable to the crank apparatus in FIG. 2A. Referring to FIG. 1A, FIG. 1B and FIG. 3A to FIG. 3C, the method of manufacturing the crank apparatus 100 by using a solid crank arm 110 in the embodiment is performed with the following steps: providing the crank arm 110 manufactured by using the material having non-uniform strain characteristic; making the thin material layer 120 having uniform strain characteristic to be in contact with the surface 115 of the crank arm 110 with the embedded surface 126; making the protruded wall 112 to cover the edge 124 of the thin material layer 120; forming at least one cavity 111 with a slightly recessed shape naturally on the surface 115 of the crank arm 110; making the thin material layer 120 to be embedded and clamped into the cavity 111 of the crank arm 110 through the covering structure extended from the protruded wall 112 while making the thin material layer 120 to retain the exposed outer surface 122; and making the sensing element 130 to be attached to the outer surface 122 of the thin material layer 120.

Figure 2A:
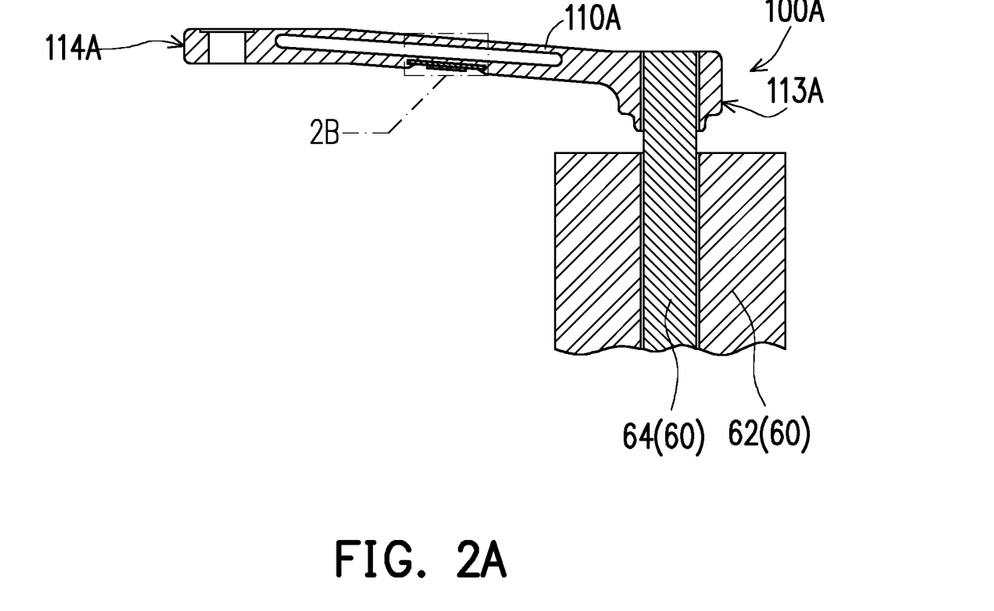
FIG. 2A is a schematic cross-sectional view of a crank apparatus according to another embodiment of the disclosure.
Figure 2B:
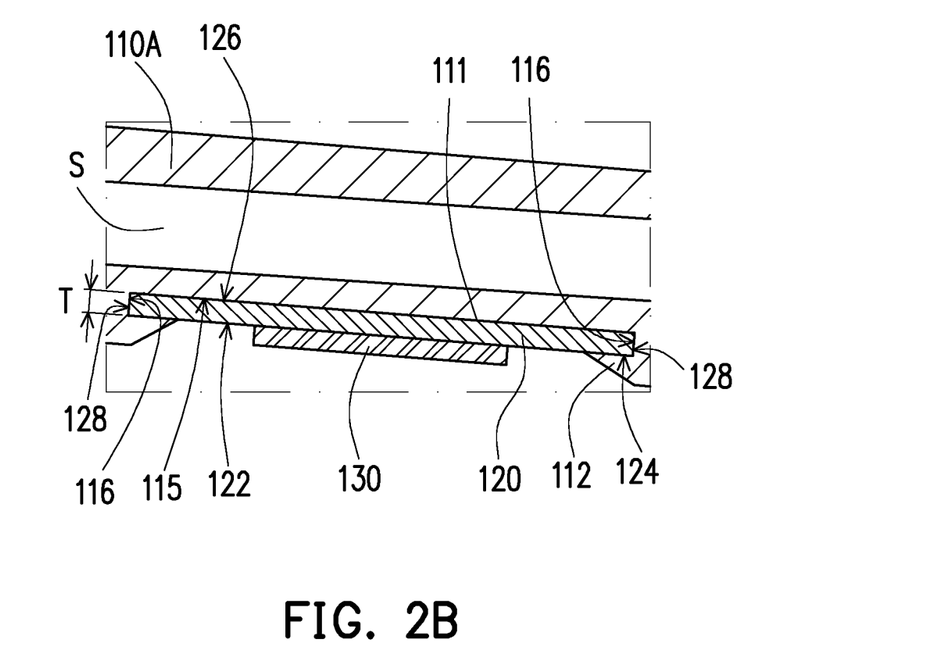
FIG. 2B is an enlarged view of the portion, labeled '2B' of FIG. 2A.
Figure 3A:
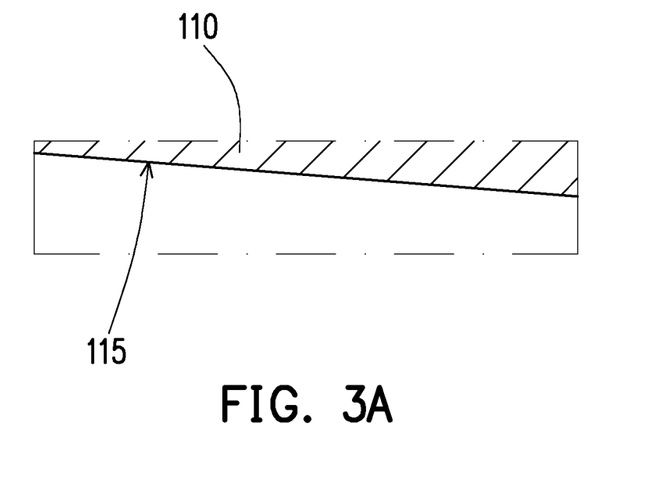
FIG. 3A to FIG. 3C is a schematic view of a manufacturing process of the crank apparatus in FIG. 1A.
Figure 3B:
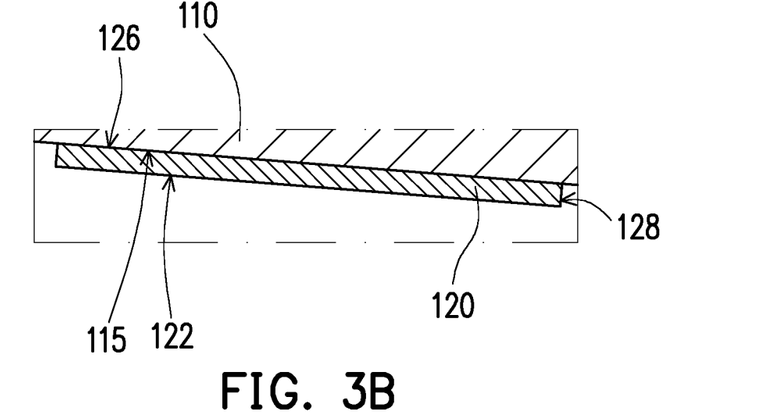
Figure 3C:
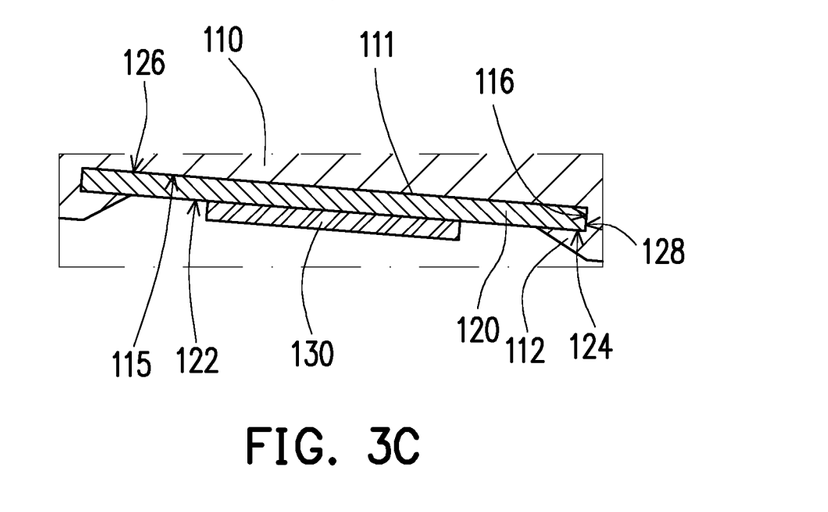

FIG. 2A is a schematic cross-sectional view of a crank apparatus according to another embodiment of the disclosure. FIG. 2B is an enlarged view of the portion, labeled '2B' of FIG. 2A. In a crank apparatus 100A of the embodiment, the same or similar reference numbers used for the crank apparatus 100 in the foregoing embodiment are adopted in the present embodiment; the present embodiment only describes the difference of the crank apparatus 100A. Referring to FIG. 2A and FIG. 2B, in the embodiment, a crank arm 110A of the crank apparatus 100A is a hollow member, but the crank arm may be a solid member in other embodiments. The interior of the crank arm 110A has a space S which may be or may not be communicated with the outer environment, such that the material of the crank arm 110A can be saved in the manufacturing process, thereby obtaining the crank apparatus 100A with light weight.

The crank apparatus 100A of the embodiment may be disposed on a bicycle, a stationary exercise bicycle or other facility suitable for pedaling, the disclosure provides no limitation thereto. For example, the crank apparatus 100A may be disposed on a stationary exercise bicycle 60. The stationary exercise bicycle 60 may include a frame 62. The frame 62 further includes a crank shaft 64 rotatably disposed thereon. A fixing end 113A of the crank arm 110A is fixed on the crank shaft 64 of the frame 62 to rotate along with the crank shaft 64, and a pedaling end 114A of the crank arm 110A may be provided with a pedal (not shown) for the user to pedal. When the user pedals on the pedal (not shown), the crank arm 110A is subjected to force and deformed. Along with the crank arm 110A which is deformed by pedaling force, therefore the thin material layer 120 to be embedded into the crank arm 11A is squeezed or stretched accordingly. Since the thin material layer 120 is embedded into the cavity 111, each of the surfaces between the crank arm 110A and the thin material layer 120 has complete and good contact with each other, such that the force applied to the crank arm 110A can be smoothly transmitted to the thin material layer 120. Besides, since the thin material layer 120 has uniform strain characteristic (or referred to as isotropy), the deformation generated by the thin material layer 120 after being subjected to force is uniform, thereby improving accuracy of the sensing element 130 in measuring the torque of the crank arm 110A. Accordingly, the pedaling force applied to the crank arm 110A can be calculated accurately such that the sensing element 130 can measure the corresponding strain of the thin material layer 120 more accurately. In other words, the target measured by the sensing element 130 is the crank arm 110A having the material with non-uniform strain characteristic (or referred to as anisotropy). The thin material layer 120 serves as a medium that transfers the force applied to the crank arm 110A to the sensing element 130. With the thin material layer 120, the non-uniform deformation transferred from the crank arm 110A to be the sensing element 130 can be changed and become isotropic by using the embedded thin material layer 120 described above, thereby improving the accuracy of the sensing element 130 in measuring the torque of the crank arm 110A. In this manner, it is possible to avoid the problem of distorted data caused by conventional sensing element that directly measures the crank arm having the material with non-uniform strain characteristic (or referred to as anisotropy). Additionally, since the thin material layer 120 inherently has uniform strain characteristic, after the user installs the crank apparatus 100A of the disclosure on the stationary exercise bicycle 60, it is not required to perform any additional calibrating action to the sensing element 130, and thus it is more convenient for the user to use the bicycle with enhanced exercise experience.

Figure 4A:
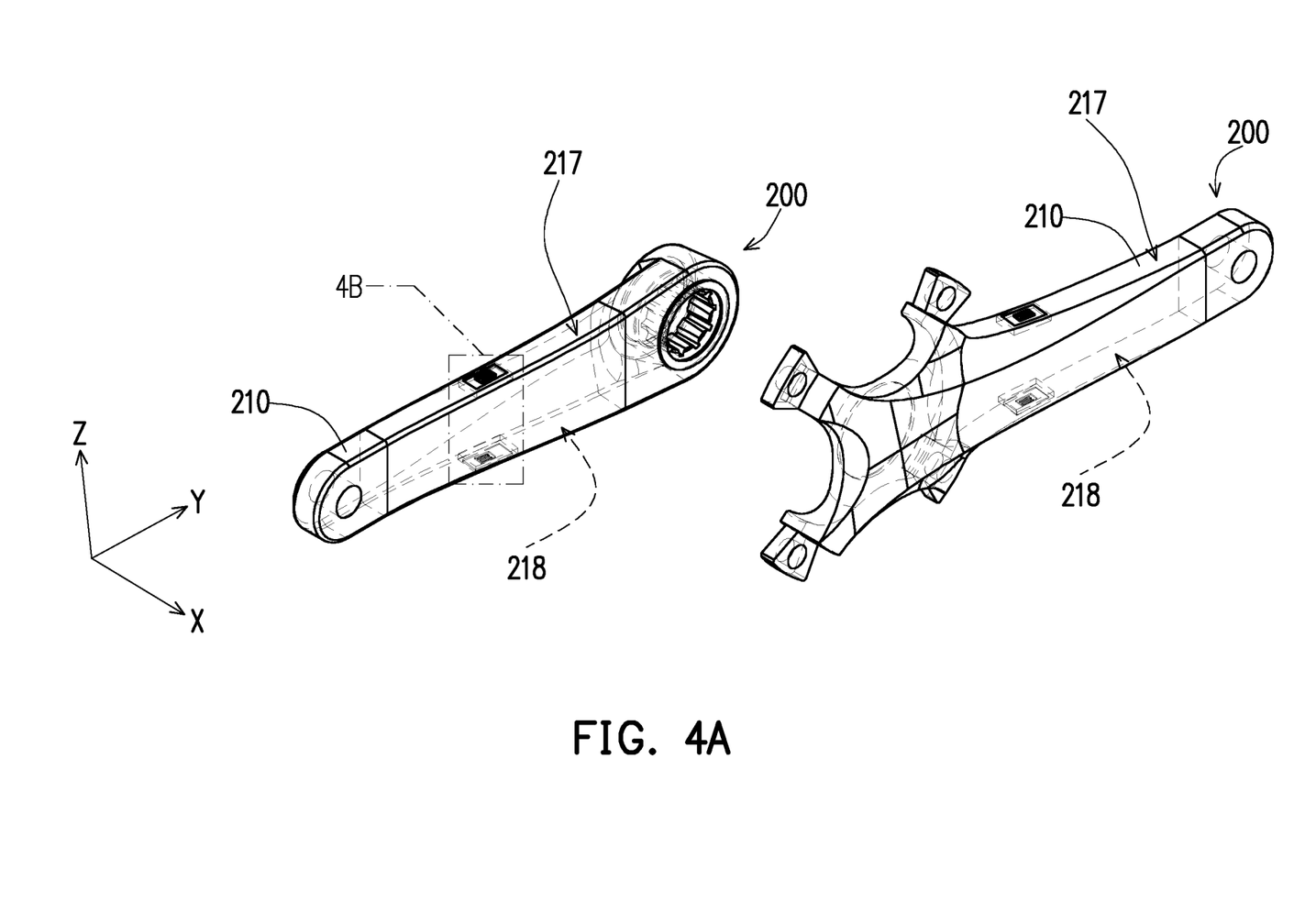
FIG. 4A is a schematic perspective view of a crank apparatus according to still another embodiment of the disclosure.
Figure 4B:
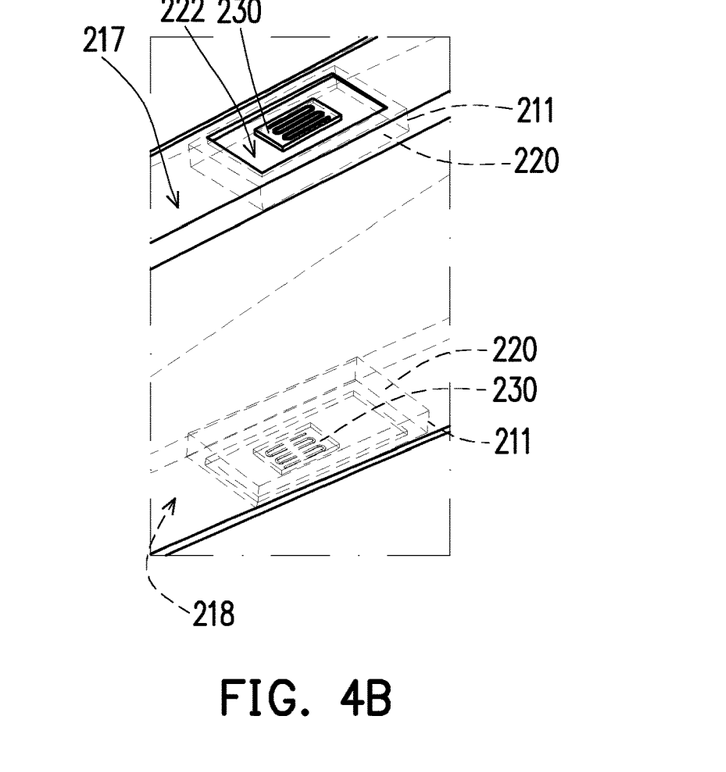
FIG. 4B is an enlarged view of the portion, labeled '4B' of FIG. 4A.
Figure 5A:
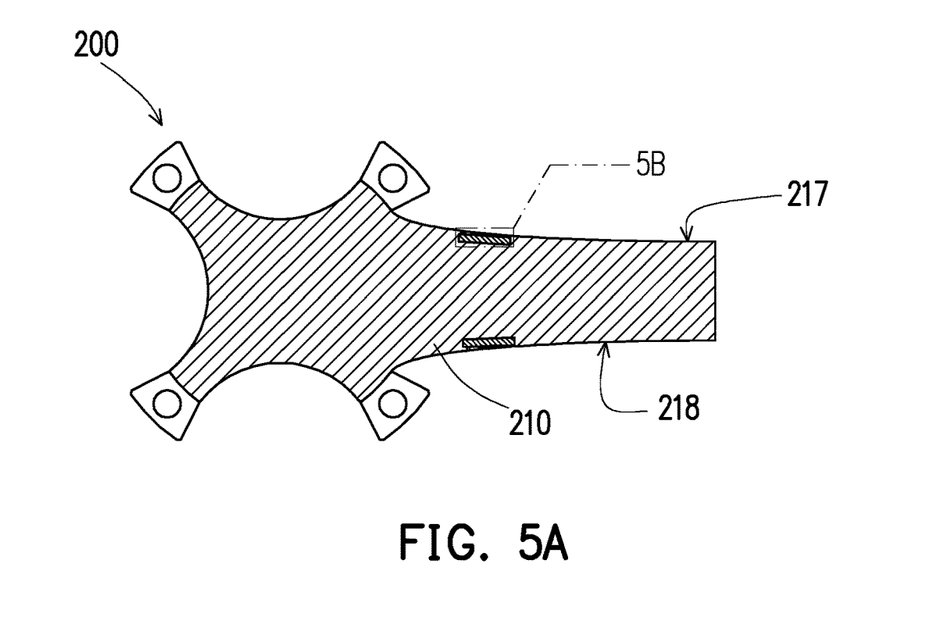
FIG. 5A is a partial schematic cross-sectional view of the crank apparatus in FIG. 4A.
Figure 5B:
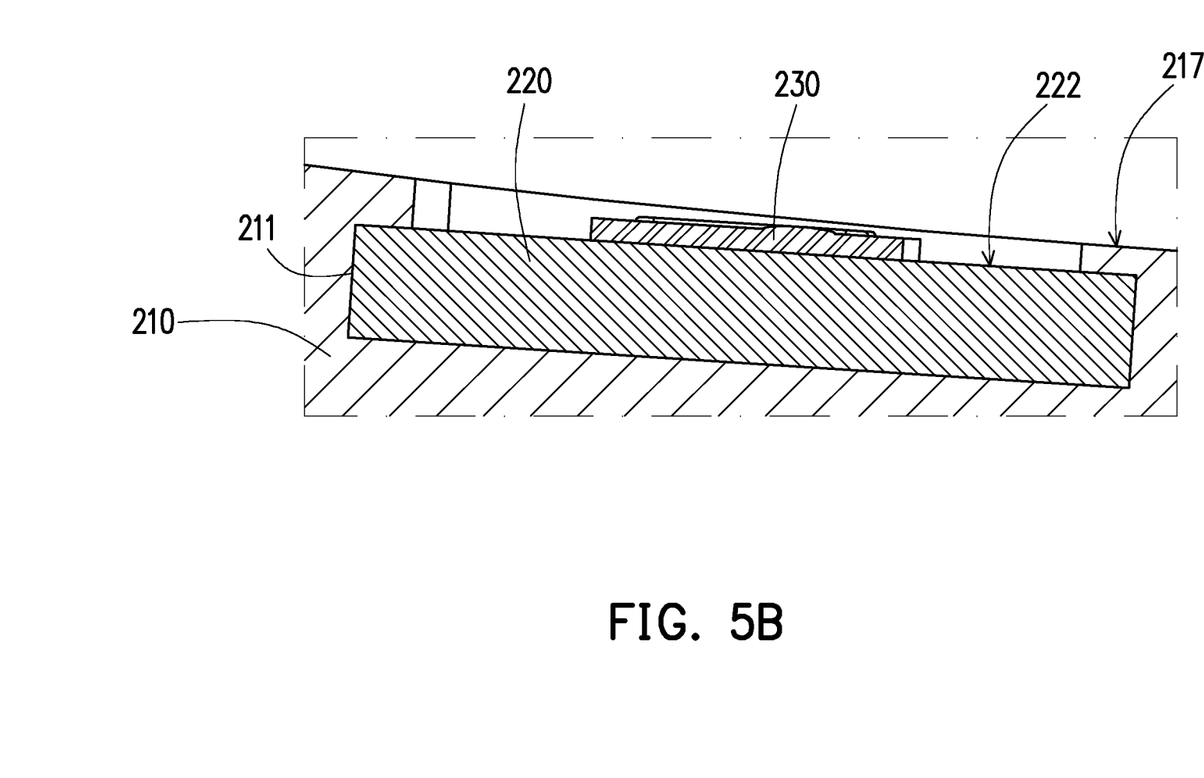
FIG. 5B is an enlarged view of the portion, labeled '5B' of FIG. 5A.

FIG. 4A is a schematic perspective view of a crank apparatus according to still another embodiment of the disclosure. FIG. 4B is an enlarged view of the portion, labeled '4B' of FIG. 4A. FIG. 5A is a partial schematic cross-sectional view of the crank apparatus in FIG. 4A. FIG. 5B is an enlarged view of the portion, labeled '5B' of FIG. 5A. In order to make illustration clear and for ease of description, FIG. 4A and FIG. 4B show the contour that is blocked by a crank apparatus 200 with dashed lines. Referring to FIG. 4A, FIG. 4B, FIG. 5A and FIG. 5B, a crank apparatus 200 includes a crank arm 210, at least one thin material layer 220 and at least one sensing element 230. The crank arm 210 has at least one cavity 211, and the cavity 211 is communicated with the outer environment. The thin material layer 220 is embedded into the cavity 211 so that the thin material layer 220 having an exposed outer surface 222. The sensing element 230 is attached to the outer surface 222 exposed by the thin material layer 220. The crank arm 210 is manufactured of a material having non-uniform strain characteristic. The thin material layer 220 is manufactured of a material having uniform strain characteristic. The crank arm 210 may be subjected to force and deformed. The thin material layer 220 may be deformed corresponding to the deformation generated by the crank arm 210. The sensing element 230 may measure the corresponding strain of the thin material layer 220, thereby calculating the force applied to the crank arm 210 according to the strain amount that is measured.

In the embodiment, the crank arm 210 includes a top surface 217 and a bottom surface 218 opposite to each other. The number of the cavity 211 is two and the cavities are respectively disposed on the top surface 217 and the bottom surface 218 of the crank arm 210. The number of the thin material layer 220 corresponding to the cavity 211 is two. The two thin material layers 220 are respectively embedded into the cavity 211 of the top surface 217 and the bottom surface 218 of the crank arm 210. The number of the sensing element 230 corresponding to the thin material layer 220 is two, the two sensing elements 230 are respectively disposed on the outer surface 222 of the thin material layer 220 in a uni-axial manner to be adapted to measure the corresponding strain of the thin material layer 220 in the uni-axial direction, that is, the changes of applied force at different positions along one of the single direction of the spatial coordinates X, Y, Z, thereby measuring the tensile strain, the compressive strain or the torsion strain of the thin material layer 220. However, the disclosure provides no limitation to the number of the sensing element 230, and the configuration number of the sensing element 230 may be selected depending on actual needs for measurement. For example, the extending direction of the sensing element 230 may be disposed in the direction parallel to Y-axis as shown in FIG. 4A and FIG. 4B, such that the sensing element 230 can measure the strain along the uni-axial direction, i.e., the Y-axial direction, thereby measuring the tensile strain, the compressive strain or the torsion strain of the thin material layer. In the embodiment, the sensing element 230 is disposed on the outer surface 222 of the thin material layer 220 in a quarter-bridge form. However, the disclosure provides no limitation to the number of the sensing element 230. The configuration number of the sensing element 230 may be selected depending on actual needs. In other embodiments, the extending direction of two sensing elements may be disposed on the top surface and bottom surface of the crank arm in parallel with the X-axial direction as shown in FIG. 4A and FIG. 4B, such that the sensing element can measure the strain along the uni-axial direction, i.e., the X-axial direction, thereby measuring the tensile strain, the compressive strain or the torsion strain of the thin material layer. Additionally, in other embodiments, the crank arm may be simultaneously provided with two sensing elements extending along X-axial direction and Y-axial direction on the top surface, such that the two sensing elements are configured in a half-bridge form on the outer surface of the thin material layer, so that the two sensing elements can measure the strain along bi-axial directions, i.e., X-axial direction and Y-axial direction, thereby measuring the tensile strain, the compressive strain, the Poisson's ratio or the torsion strain of the thin material layer. Similarly, in other embodiments, the crank arm may be simultaneously provided with two sensing elements extending along X-axial direction and Y-axial direction on the bottom surface, such that the two sensing elements are configured in a half-bridge form on the outer surface of the thin material layer, so that the two sensing elements can measure the strain along bi-axial directions, i.e., X-axial direction and Y-axial direction, thereby measuring the tensile strain, the compressive strain, the Poisson's ratio or the torsion strain of the thin material layer. It should be indicated that, for ease of description, FIG. 4A shows spatial coordinates X, Y, Z for exemplary purpose, the directions along which the sensing element 230 actually measures are not limited to the directions X, Y, Z shown in FIG. 4A but depends on actual needs.

Figure 6A:
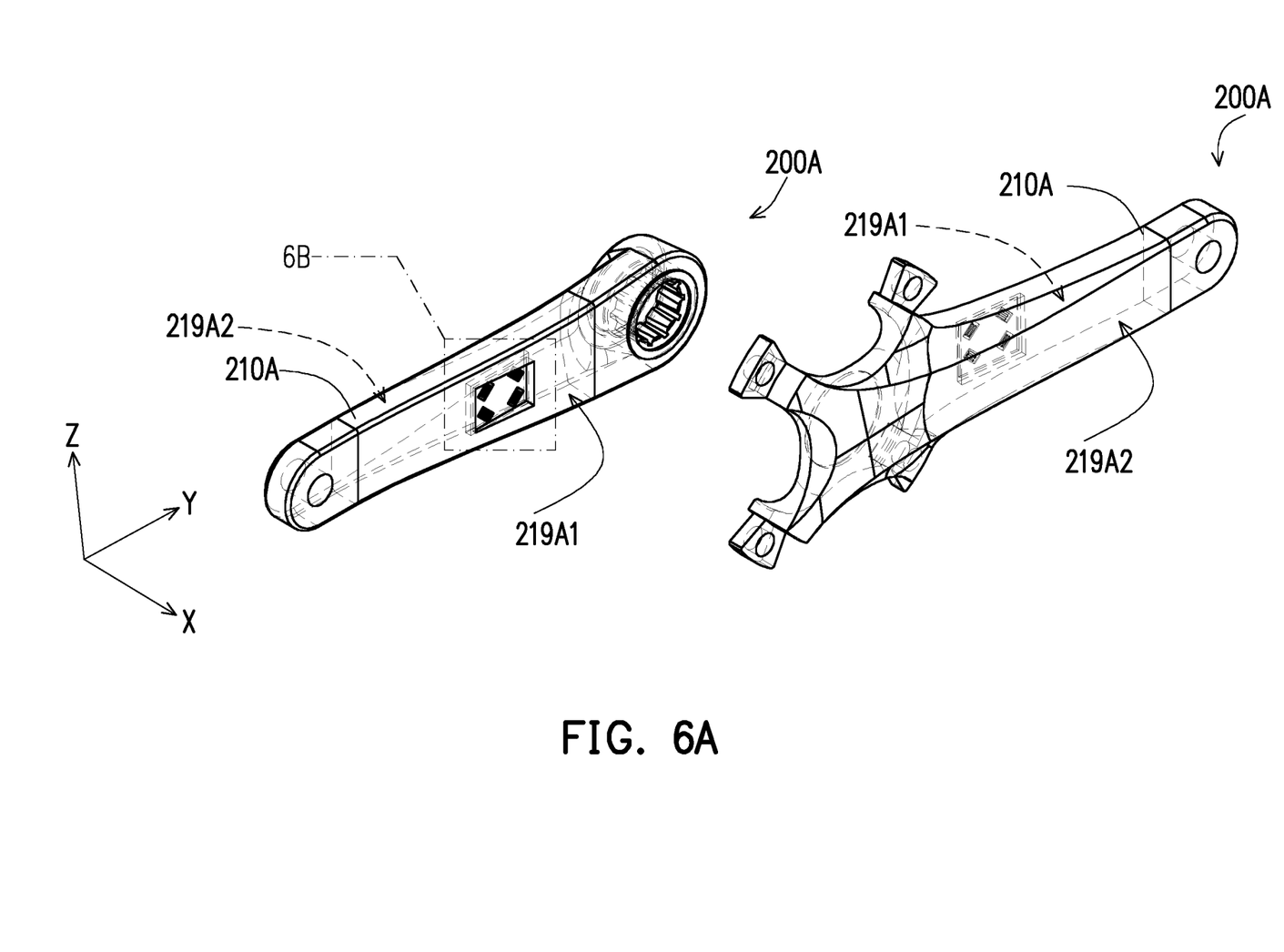
FIG. 6A is a schematic perspective view of a crank apparatus according to yet another embodiment of the disclosure.
Figure 6B:
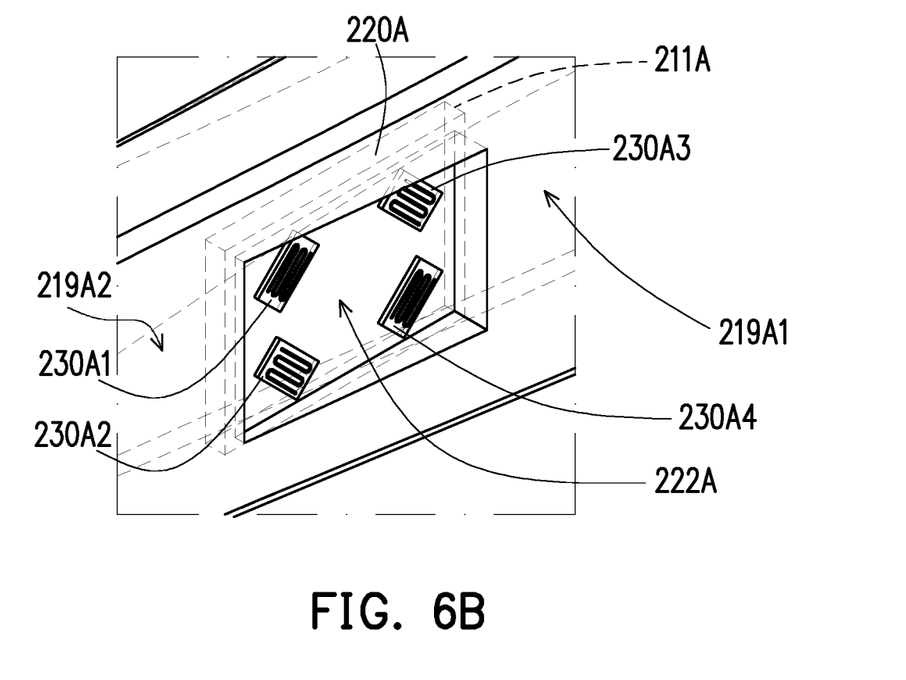
FIG. 6B is an enlarged view of the portion, labeled '6B' of FIG. 6A.
Figure 7A:
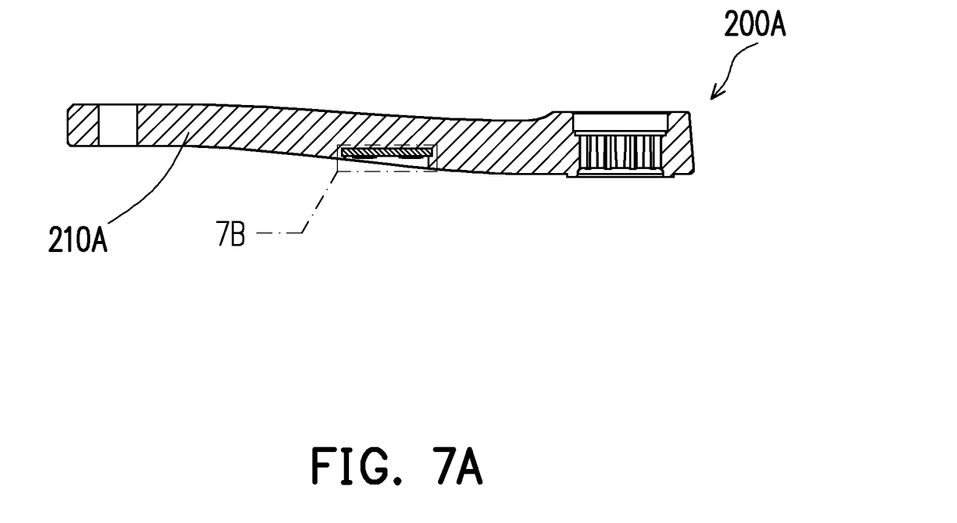
FIG. 7A is a partial schematic cross-sectional view of the crank apparatus in FIG. 6A.
Figure 7B:
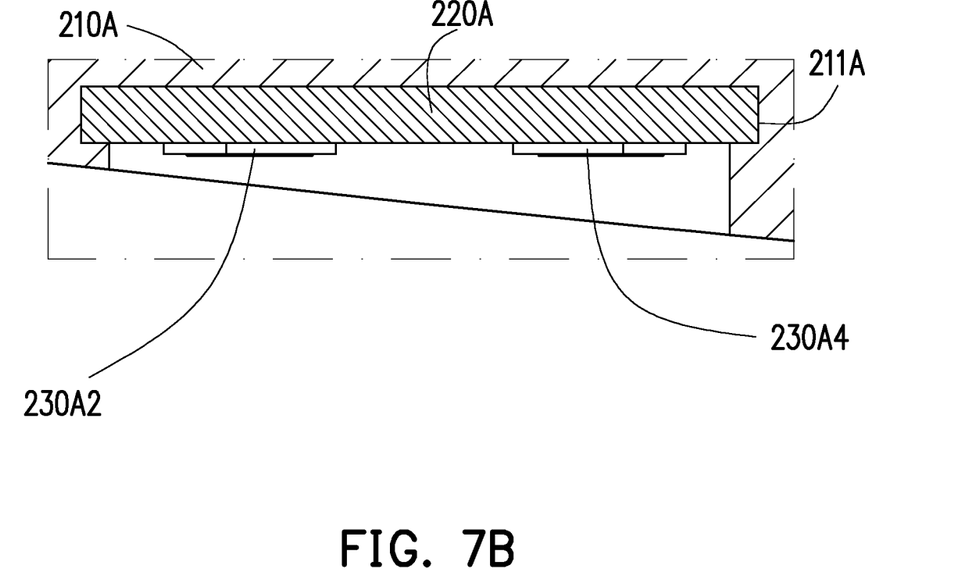
FIG. 7B is an enlarged view of the portion, labeled '7B' of FIG. 7A.

FIG. 6A is a schematic perspective view of a crank apparatus according to yet another embodiment of the disclosure. FIG. 6B is an enlarged view of the portion, labeled '6B' of FIG. 6A. FIG. 7A is a partial schematic cross-sectional view of the crank apparatus in FIG. 6A. FIG. 7B is an enlarged view of the portion, labeled '7B' of FIG. 7A. In a crank apparatus 200A of the embodiment, the same or similar reference numbers used for the crank apparatus 200 in the foregoing embodiment are adopted in the present embodiment; the present embodiment only describes the difference of the crank apparatus 200A. In order to make the illustration clear and for ease of description, FIG. 6A and FIG. 6B show the contour blocked by the crank apparatus 200A in dashed lines. Referring to FIG. 6A, FIG. 6B, FIG. 7A and FIG. 7B, in the embodiment, a crank arm 210A includes two lateral surfaces 219A1 and 219A2 opposite to each other. The number of cavity 211A included in the crank arm 210A is one and the cavity 211A is disposed on the lateral surface 219A1 of the crank arm 210A. The number of the thin material layer 220A corresponding to the cavity 211A is one. The thin material layer 220A is embedded into a position suitable for measuring change of the corresponding strain characteristics on the lateral surface 219A1 of the crank arm 210A. An outer surface 222A of the thin material layer 220A is provided with four sensing elements 230A1, 230A2, 230A3 and 230A4. The four sensing elements 230A1, 230A2, 230A3 and 230A4 are arranged on the outer surface 222A of the thin material layer 220A at an angle that is about 45 degrees, thereby measuring the change of component of force that is applied in at least two spatial directions (i.e., bi-axial direction). In other words, the above-mentioned configuration is suitable for measuring the corresponding strain of the thin material layer 220A that is applied to force along any two orthogonal axial directions (i.e., coplanar to XY, YZ or XZ in space). However, the disclosure provides no limitation to the number of the sensing element, and the configuration number of the sensing element may be selected depending on the actual needs for measurement. In the embodiment, the sensing elements 230A1, 230A2, 230A3 and 230A4 are disposed on the outer surface 222A of the thin material layer 220A in a full-bridge form. However, the disclosure provides no limitation to the number of the sensing element, and the configuration number of the sensing element may be selected depending on the actual needs. It should be indicated that, for ease of description, FIG. 6A shows the spatial coordinates X, Y, Z for exemplary purpose. The directions along which the sensing elements 230A1, 230A2, 230A3 and 230A4 actually measure are not limited to the directions X, Y, Z shown in FIG. 6A but depend on actual needs.

It should be indicated that, in the embedment, the sensing elements 230A1 and 230A2 are disposed on the outer surface 222A of the thin material layer 220A in bi-axial manner, and the sensing elements 230A3 and 230A4 are disposed on the outer surface 222A of the thin material layer 220A in bi-axial manner. In other words, the sensing elements 230A1, 230A2, 230A3 and 230A4 are disposed on the outer surface 222A of the thin material layer 220A in two sets configured in bi-axial manner or in a full-bridge form to be adapted to measure the corresponding strain of the thin material layer 220A along any two orthogonal axial directions, thereby obtaining the tensile strain, the compressive strain, the Poisson's ratio or torque change of the thin material layer 220A. For example, the extending direction of the sensing elements 230A1 and 230A2 may be any two perpendicular axial directions respectively disposed on the YZ plane as shown in FIG. 6A and FIG. 6B. Similarly, the extending direction of the sensing elements 230A3 and 230A4 may be any two perpendicular axial directions respectively disposed on the YZ plane as shown in FIG. 6, and it is not limited that the sensing elements 230A1, 230A2, 230A3 and 230A4 are disposed along the Y-axial direction or Z-axial direction, the configuration may be set depending on the needs. In other embodiments, four sensing elements or two sensing elements may be disposed on at least one of the two lateral surfaces 219A1 and 219A2 of the crank device 200A shown in FIG. 6A and FIG. 6B along Z-axial direction and Y-axial direction in a full-bridge form or in a half-bridge form respectively, and one sensing element may be disposed on at least one of the top surface 217 or the bottom surface 218 of the crank device 200 shown in FIG. 4A and FIG. 4B along the X-axial direction in a quarter-bridge form, so as to be adapted to measure the strain along three axial directions (X, Y, Z axial directions) of the thin material layer, thereby measuring the tensile strain, the compressive strain, the Poisson's ratio or the torsion strain of the thin material layer. The actual measuring directions of various sensing elements are not limited to the X, Y, Z directions shown in FIG. 6 or FIG. 4 and may be set depending on actual requirement.

Figure 8A:
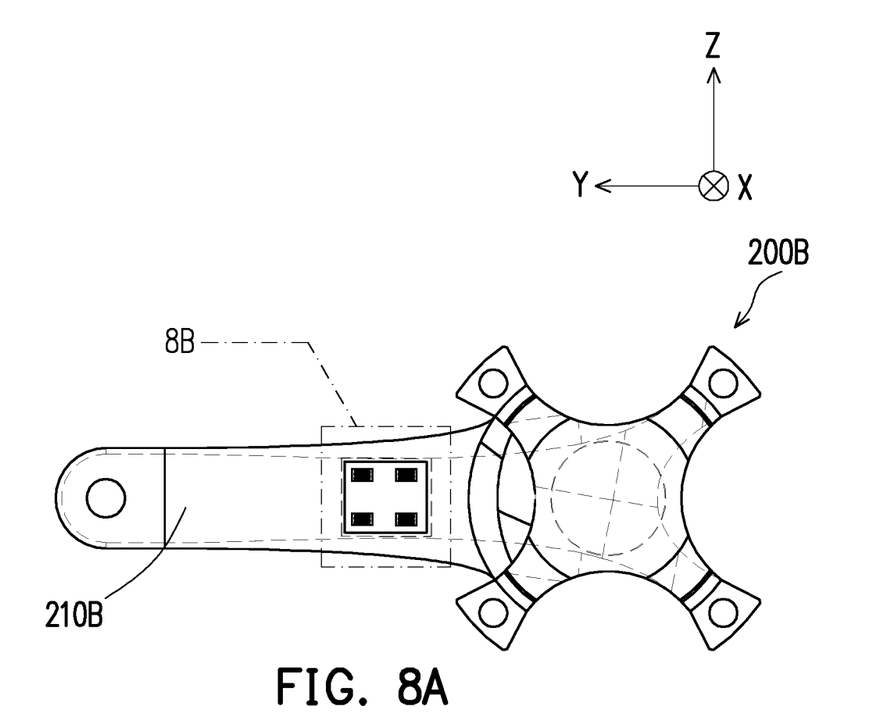
FIG. 8A is a schematic perspective view of a crank apparatus according to yet another embodiment of the disclosure.
Figure 8B:
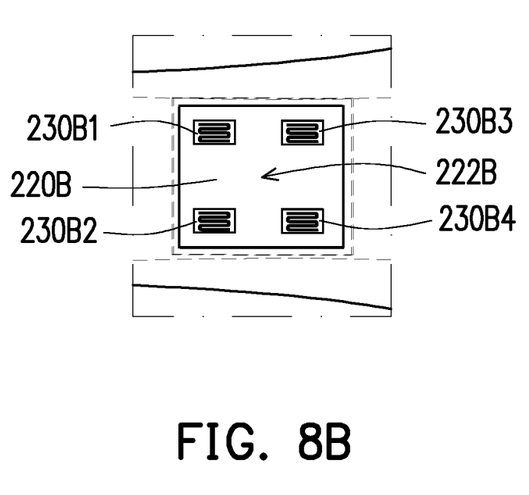
FIG. 8B is an enlarged view of portion, labeled '8B' of FIG. 8A.

FIG. 8A is a schematic perspective view of a crank apparatus according to yet another embodiment of the disclosure. FIG. 8B is an enlarged view of portion, labeled '8B' of FIG. 8A. In a crank apparatus 200B of the embodiment, the same or similar reference numbers used for the crank apparatus 200 in the foregoing embodiment are adopted in the present embodiment; the present embodiment only describes the difference of the crank apparatus 200B. In order to make the illustration clear and for ease of description, FIG. 8A and FIG. 8B show the contour blocked by the crank apparatus 200B in dashed lines. Referring to FIG. 8A and FIG. 8B, sensing elements 230B1, 230B2, 230B3 and 230B4 are disposed on an outer surface 222B of a thin material layer 220B in parallel in bi-axial manner to be adapted to measure the corresponding strain of the thin material layer 220B at different positions along a single direction, thereby obtaining the tensile strain, the compressive strain or the torsion strain of the thin material layer 220B. However, the disclosure provides no limitation to the number and configuration of the sensing element, and number and configuration of the sensing element may be selected depending on actual needs for measurement. In the embodiment, the sensing elements 230B1, 230B2, 230B3 and 230B4 are disposed on the outer surface 222B of the thin material layer 220B in a full-bridge manner. However, the disclosure provides no limitation to the number and configuration of the sensing element, and number and configuration of the sensing element may be selected depending on actual needs for measurement. In the embodiment, the sensing elements 230B1, 230B2, 230B3 and 230B4 are disposed on the outer surface 222B of the thin material layer 220B in a full-bridge form, thereby achieving a better measuring sensitivity. It should be indicated that, for ease of description, FIG. 8A shows the spatial coordinates X, Y, Z for exemplary purpose. The directions along which the sensing elements 230B1, 230B2, 230B3 and 230B4 actually measure are not limited to the directions X, Y, Z shown in FIG. 8A but depend on actual needs.

In summary, in the crank apparatus of the disclosure, the crank arm is manufactured of a material having non-uniform strain characteristic. The thin material layer is manufactured of a material having uniform strain characteristic. The thin material layer is embedded into the cavity. Each of the surfaces between the crank arm and the thin material layer has complete and good contact with each other such that the force that is applied to the crank arm can be smoothly transmitted to the thin material layer. When the user pedals on the pedal, the crank arm is subjected to force and deformed. Along with the crank arm which is deformed by pedaling force, therefore the thin material layer to be embedded into the crank arm is squeezed or stretched accordingly. The sensing element may measure the force applied to the crank arm through the thin material layer serving as a medium for transferring force. Since the deformation generated by the thin material layer after being subjected to force is uniform, the accuracy of the sensing element in measuring the corresponding strain of the thin material layer is improved. In this manner, it is possible to avoid the problem of distorted data caused by conventional sensing element that directly measures the crank arm having the material with non-uniform strain characteristic (or referred to as anisotropy). Additionally, since the thin material layer inherently has uniform strain characteristic, after the crank apparatus of the disclosure is disposed on the bicycle or the stationary exercise bicycle, it is not required to perform any additional calibrating action to the sensing element, and thus it is more convenient for the user to use the bicycle with enhanced exercise experience.

Although the disclosure has been disclosed by the above embodiments, the embodiments are not intended to limit the disclosure. It will be apparent to those skilled in the art that various modifications and variations can be made to the structure of the disclosure without departing from the scope or spirit of the disclosure. Therefore, the protecting range of the disclosure falls in the appended claims.

What is claimed is:

1. A crank apparatus, comprising:
a crank arm, having at least one cavity on a surface of the crank arm;
at least one thin material layer, embedded into the at least one cavity, and having an exposed outer surface, an embedded surface disposed on another surface of the at least one thin material layer relatively away from the exposed outer surface, and a plurality of lateral surfaces respectively connected between the exposed outer surface and the embedded surface, and the embedded surface and the plurality of lateral surfaces of the at least one thin material layer correspondingly contact a plurality of surfaces of the at least one cavity of the crank arm; and
at least one sensor, attached to the exposed outer surface of the at least one thin material layer, wherein the crank arm is manufactured of a composite material having non-uniform strain characteristic, the at least one thin material layer is manufactured of a material having uniform strain characteristic, the crank arm is adapted to be subjected to force and deformed, the at least one thin material layer is adapted to be deformed corresponding to the deformation of the crank arm, the at least one sensor is adapted to measure the corresponding strain of the at least one thin material layer caused by a force applied to the crank arm,
wherein the at least one cavity of the crank arm comprises a plurality of protruded walls respectively covering at least one edge of the exposed outer surface of the at least one thin material layer, wherein the movement of the at least one thin material layer along any three orthogonal axial directions in the crank arm is limited by the plurality of protruded walls.

2. The crank apparatus according to claim 1, wherein the at least one sensor is at least one strain gauge or a pressure sensor.

3. The crank apparatus according to claim 2, wherein the at least one strain gauge is disposed on the outer surface of the thin material layer in a uni-axial manner, the at least one strain gauge is adapted to measure the corresponding strain of the thin material layer along a uni-axial direction.

4. The crank apparatus according to claim 2, wherein the number of the at least one strain gauge is at least two, the at least two strain gauges are disposed on the outer surface of the at least one thin material layer in a bi-axial manner, the at least two strain gauges are adapted to measure the corresponding strain of the at least one thin material layer along any two orthogonal axial directions.

5. The crank apparatus according to claim 2, wherein the number of the at least one strain gauge is at least three, the at least three strain gauges are disposed on the outer surface of the at least one thin material layer in a tri-axial manner, the at least three strain gauges are adapted to measure the corresponding strain of the at least one thin material layer along three orthogonal axial directions.

6. The crank apparatus according to claim 2, wherein the at least one strain gauge is disposed on the outer surface of the at least one thin material layer in a quarter-bridge form.

7. The crank apparatus according to claim 2, wherein the at least one strain gauge is disposed on the outer surface of the at least one thin material layer in a half-bridge form.

8. The crank apparatus according to claim 2, wherein the at least one strain gauge is disposed on the outer surface of the at least one thin material layer in a full-bridge form.

9. The crank apparatus according to claim 1, wherein the crank arm is a solid member.

10. The crank apparatus according to claim 1, wherein the crank arm is a hollow member.

11. The crank apparatus according to claim 1, wherein the composite material comprises any one of a non-metal-and-non-metal composite material, a non-metal-and-metal composite material, and a metal-and-metal composite material.

12. The crank apparatus according to claim 1, wherein a material of the crank arm comprises any one of a carbon fiber, a glass fiber, a Kevlar fiber, a Dyneema fiber, a plant fiber, a boron fiber, an aramid fiber, a silicon carbide fiber, asbestos fabrics, a monocrystalline whisker, a metal wire and hard particles or a composite material consisting of a mixture of any two of the above.

13. The crank apparatus according to claim 1, wherein the at least one thin material layer is a single material having uniform strain characteristic.

14. The crank apparatus according to claim 1, wherein the material of the at least one thin material layer comprises a metal, a plastic or a flexible glass.

15. The crank apparatus according to claim 1, wherein the at least one thin material layer is subjected to a surface treatment process to form a roughened surface, the surface treatment process is configured to any one of a sand-blasting process, a texture-treatment process, a laser-treatment process, a plasma-treatment process, a chemical-treatment process.

16. The crank apparatus according to claim 1, wherein a thickness of the at least one thin material layer is within a range between 0.1 mm and 1.85 mm.

17. A bicycle, comprising:
a frame, comprising a crank shaft; and
the crank apparatus claimed in claim 1, wherein the crank arm is fixed on the crank shaft, the crank arm is adapted to be pedaled by a user and deformed by the force.

18. A stationary exercise bicycle, comprising:
a frame, comprising a crank shaft; and
the crank apparatus claimed in claim 1, wherein the crank arm is fixed on the crank shaft, the crank arm is adapted to be pedaled by a user and deformed by the force.

* * * * *